United States Patent
Gupta et al.

(10) Patent No.: US 12,337,019 B2
(45) Date of Patent: *Jun. 24, 2025

(54) VEHICLES FOR APPLYING BACTERIA TO SKIN, SCALP, AND HAIR

(71) Applicants: Northwestern University, Evanston, IL (US); Yobee Care, Inc., Chicago, IL (US)

(72) Inventors: Ruchi Gupta, Chicago, IL (US); Tarun Jain, Chicago, IL (US)

(73) Assignees: Northwestern University, Evanston, IL (US); Yobee Care, Inc., Chicago, IL (US)

(*) Notice: Subject to any disclaimer, the term of this patent is extended or adjusted under 35 U.S.C. 154(b) by 784 days.

This patent is subject to a terminal disclaimer.

(21) Appl. No.: 17/461,347

(22) Filed: Aug. 30, 2021

(65) Prior Publication Data

US 2021/0386803 A1 Dec. 16, 2021

Related U.S. Application Data

(63) Continuation-in-part of application No. 16/474,950, filed as application No. PCT/US2017/068765 on Dec. 28, 2017, now Pat. No. 11,103,544.

(60) Provisional application No. 62/440,797, filed on Dec. 30, 2016.

(51) Int. Cl.
| | |
|---|---|
| *A61K 35/747* | (2015.01) |
| *A61K 9/00* | (2006.01) |
| *A61K 31/714* | (2006.01) |
| *A61K 36/9066* | (2006.01) |
| *A61K 45/06* | (2006.01) |
| *A61K 47/10* | (2017.01) |
| *A61K 47/44* | (2017.01) |
| *A61K 47/46* | (2006.01) |
| *A61P 17/00* | (2006.01) |

(52) U.S. Cl.
CPC .......... *A61K 35/747* (2013.01); *A61K 9/0014* (2013.01); *A61K 31/714* (2013.01); *A61K 36/9066* (2013.01); *A61K 45/06* (2013.01); *A61K 47/10* (2013.01); *A61K 47/44* (2013.01); *A61K 47/46* (2013.01); *A61P 17/00* (2018.01)

(58) Field of Classification Search
None
See application file for complete search history.

(56) References Cited

U.S. PATENT DOCUMENTS

| | | |
|---|---|---|
| 2009/0232785 A1 | 9/2009 | Breton |
| 2014/0037688 A1 | 2/2014 | Berkes et al. |
| 2016/0243057 A1 | 8/2016 | McWherter et al. |

FOREIGN PATENT DOCUMENTS

| | | | |
|---|---|---|---|
| CN | 105031576 A | * | 11/2015 |
| CN | 105815727 A | * | 8/2016 |
| KR | 20160049812 A | | 5/2016 |
| WO | 2011109469 A1 | | 9/2011 |
| WO | 2012118535 A1 | | 9/2012 |

OTHER PUBLICATIONS

European Patent Office, Examination Report 94(3) EPC issued in related foreign application 177889075.2 on May 17, 2023, 5 pages.
Stücker M, et al. "Topical vitamin B12—a new therapeutic approach in atopic dermatitis-evaluation of efficacy and tolerability in a randomized placebo-controlled multicentre clinical trial", Br J Dermatol. Apr. 30, 2004;150(5):977-83.
McLoone P, et al. "Honey: A Therapeutic Agent for Disorders of the Skin", Central Asian Journal of Global Health, vol. 5, No. 1, Aug. 4, 2016, 17 pages.
Vaugh A.R., et al. "Effects of Turmeric (*Curcuma longa*) on Skin Health: A Systematic Review of the Clinical Evidence", Physiotherapy Research, vol. 30, No. 8, May 23, 2016, pp. 1243-1264.
Xiao A, et al. "Novel Topical Treatment for Dandruff & Dry Scalp Through Sustained Balance in Skin Microbiome", Clin Cosmet Investig Dermatol. Jul. 24, 2021;14:945-947.
Database WPI. Week 201639. Thomson Scientific, London, BG; AN 2016-30398D & KR 2016 0049812 A (Korean Cosmetics Co Ltd) May 10, 2016.
European Patent Office. Extended European Search Report for application 177889075.2. Mailed on Jun. 15, 2020.
Eminence Clear Skin Probiotic Moisturizer. Available for sale as of Dec. 1, 2016. Accessed on Mar. 4, 2020. https://www.amazon.com/gp/product/B005LZT9GU/ref=as_li_tl?e=UTF8&camp=1789&creative=390957&creativeASIN=B005LZT9GU&linkCode=as2&tag=palforwom-20.
International Searching Authority, International Search Report and Written Opinion for application PCT/US2017/068765, mailed on Mar. 6, 2018.
Suslov A.B. I dr. Inaktivatsiya microoramizmov v srede cverxkriticheskogo CO2. Sverxkriticheskie Fluidy: Teoriya I Praktika. 2008, Tom 3, No. 3 p. 3, paragraph 2. With machine translation.

(Continued)

*Primary Examiner* — David W Berke-Schlessel
(74) *Attorney, Agent, or Firm* — J. Peter Paredes; Amin Wasserman Gurnani LLP

(57) ABSTRACT

Disclosed are methods and topical compositions for applying bacteria to skin, scalp and hair. The topical compositions include bacteria in a suitable base vehicle comprising honey for applying the bacteria to skin, scalp and hair. The base vehicle may include additional components such as, but not limited to, plant-based products, micro-nutrients, emollients and plant-sourced emulsifiers, and anti-oxidants, among other components. The topical compositions may be utilized in methods for treating and/or preventing skin, scalp, and hair conditions such as, but not limited to, dry skin, dry scalp, dandruff, psoriasis, cradle cap, seborrheic dermatitis, and/or eczema.

20 Claims, No Drawings

(56) References Cited

OTHER PUBLICATIONS

Epicuren Acidophilus Probiotic Facial Cream. Available for sale as of Dec. 1, 2016. Accessed online at https://www.amazon.co.uk/Epicuren-Acidophilus-Probiotic-Facial-Cream/dp/B000ULF98W on Mar. 4, 2020.

* cited by examiner

VEHICLES FOR APPLYING BACTERIA TO SKIN, SCALP, AND HAIR

CROSS-REFERENCE TO RELATED APPLICATIONS

The present applications claims priority from and is a continuation-in-part from U.S. patent application Ser. No. 16/474,950, filed Jun. 28, 2019, which claims priority from PCT application serial no. PCT/US2017/068765, filed Dec. 28, 2017, which claims priority from U.S. Provisional Application No. 62/440,797, filed on Dec. 30, 2016, all herein incorporated by reference in their entireties.

BACKGROUND

The present invention relates to methods and compositions for introducing bacteria to the skin, scalp, and hair. Specifically, the invention relates to topical compositions that include honey and may be utilized as vehicles for introducing bacteria to the skin, scalp, and hair. In addition to honey, the disclosed topical compositions may include plant-based lipids, micro-nutrients, emollients and plant-sourced emulsifiers, and anti-oxidants, among other components.

The health and character of the skin is an area of concern for a large portion of the population. Beyond the barrier functions the skin provides, it is also responsible for conveying sense information, and—very literally—presenting its wearer to the world. Healthy skin may therefore support one or more of these functions, potentially preventing physical or psychological injury. The skin is a living organ, and should be treated as such. The present invention provides a vehicle to take advantage of this reality, among other things. Billions of dollars are spent every year by people who wish to improve the appearance of their skin, either through their diet, cosmetics, or by some other means.

Presently, many products aimed at improving the health and structure of the skin exist. However, these products are characterized by several limitations. First, and most importantly, these products may not be characterized as being "skin microbiome friendly." The skin is a living part of an intricate web of human cells and microorganisms, and the products presently available are not entirely supportive or compatible with the skin microbiome and pH. Of the multitude of current topical preparations, none are in biological parity with their purported target. Evidence continues to accumulate that nurturing the skin pH and its biome can be beneficial to the skin's condition.

An additional limitation of current topical preparations is their dependence on pharmaceutical agents, synthetic detergents, and the use of skin-irritating preservatives, biocides and solvents. While useful in preparing mass-market skincare products, the inclusion of skin irritating or compromising chemicals in a preparation aimed at improving skin quality represents a contradiction. For example, in order to treat moderate to severe cases of eczema or psoriasis, the current standard of care revolves around the use of corticosteroids, immunosuppressants, ultraviolet radiation, and similar measures. These treatments are not only often expensive, but carry large side-effect profiles, and substantial risk to their recipients. Even in the case of healthy individuals aiming to improve the cosmetic character or general health of their skin, the ingredients in many preparations are at odds with the user's goals.

There is therefore a need for improvement over the shortcomings of skincare products, in the form of a shelf-stable, nutrient-rich solution, which delivers bacteria to the skin. The present invention consists of a vehicle and associated bacterial preparation, aimed at viable application of said bacteria to the skin, scalp, and hair.

SUMMARY OF THE INVENTION

Disclosed are methods and topical compositions for applying bacteria to skin, scalp and hair. The topical compositions include bacteria in a suitable base vehicle comprising honey for applying the bacteria to skin, scalp and hair. In addition to honey, the base vehicle may include components such as, but not limited to, plant-based products, micro-nutrients, emollients and plant-sourced emulsifiers, and anti-oxidants, among other components. The disclosed topical compositions are formulated to be supportive and compatible with the skin microbiome and pH. The topical compositions may be utilized in methods for treating and/or preventing skin, scalp, and hair conditions such as, but not limited to, dry skin, dry scalp, dandruff, psoriasis, cradle cap, seborrheic dermatitis, and/or eczema.

The methods and compositions are set forth in part in the description which follows, and in part will be obvious from the description, or can be learned by practice of the methods and compositions. The advantages of the methods and compositions will be realized and attained by means of the elements and combinations particularly pointed out in the appended claims. It is to be understood that both the foregoing general description and the following detailed description are exemplary and explanatory only and are not restrictive of the methods and compositions, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, a "subject in need thereof" may include a subject in need of skin, scalp, or hair care and/or treatment. A subject in need thereof may include, but is not limited to, a subject having or at risk for developing one or more of dry skin, dry scalp, dandruff, psoriasis, cradle cap, seborrheic dermatitis, and/or eczema.

As used herein, the term "subject" may be used interchangeable with the terms "patient" and "individual." A subject may include a human and/or a non-human animal (e.g., a companion animal such as a dog or a cat).

Disclosed are methods and topical compositions for applying bacteria to the skin, scalp, and/or hair. Accordingly, in the methods and topical compositions the bacteria are formulated in a suitable base vehicle comprising honey for applying bacteria to the skin, scalp, and hair as a topical composition. The disclosed topical compositions preferably are formulated to be supportive and compatible with the skin microbiome and pH.

In particular, the base vehicle may include honey as produced by honey bees including, but not limited to, honey produced by any species of the genus Apis such as *A. mellifera, A. cerana, A. florea, A. andreniformis, A. koschevnikovi,* and *A. dorsata.* The base vehicle may include honey produced by honey bees and collected pollen and nectar from any flowering plant, in particular, honey produced from the pollen and nectar of *Leptospermum scoparium* and its relatives and/or the Manuka tree or its relatives (i.e., Manuka honey). Suitable honey for the disclosed topical compositions may include raw honey or processed honey. In some embodiments, honey used in the disclosed compositions has been heat-treated (e.g., via pasteurization) and/or irradiated.

The disclosed topical compositions include a suitable concentration of honey, for example, to prepare a composition for treating and/or preventing skin conditions and/or scalp conditions. In some embodiments, the honey may be present in the disclosed compositions at a concentration of at least about 1%, 2%, 3%, 5%, 7%, 10%, 15%, 20%, 25%, 30%, 35%, 40%, 45%, 50%, 55%, 60%, 65%, 70% (w/w) or higher, or within a range bounded by any of these values (e.g. about 15-60% (w/w) or 20-50% (w/w)).

The disclosed topical compositions include bacteria which may be live bacteria and/or killed bacterial. Killed bacteria for the disclosed compositions may be killed by methods known in the art, including but not limited to heat-treatment, irradiations, and/or chemical treatment. In some embodiments, the bacteria are present in the topical composition at a concentration of at least about $10^4$, $10^5$, $10^6$, $10^7$, $10^8$ colony forming units (CFU)/gram (g) topical composition or higher, or within a concentration range bounded by any of these values (e.g., $10^4$-$10^8$ CFU/g). Where the bacteria are killed bacteria, the concentration of the bacteria added to the composition may be determined prior to killing the bacteria. In other embodiments, the bacteria are present at a concentration of at least about $10^{-8}$, $10^{-7}$, $10^{-6}$, $10^{-5}$, $10^{-4}$ g bacteria/g composition or higher, or within a concentration range bounded by any of these values (e.g., $10^{-7}$-$10^{-8}$ bacteria/g composition). In other embodiments, the bacteria are present at a concentration of at least about 1%, 2%, 3%, 5%, 7%, 10%, 15%, 20% (w/w) or higher or within a range bounded by any of these values (e.g., at a concentration of 3-10% (w/w)).

In some embodiments, bacteria for the disclosed topical compositions may include bacteria suitable for use in a topical formulation for treating and/or preventing skin conditions and/or scalp conditions. Suitable bacteria for the disclosed compositions may include, but are not limited to bacteria of the genera *Lactobacillus, Bifidobacterium,* or *Streptococcus,* especially *Lactobacillus acidophilus, Lactobacillus Plantarum, Lactobacillus rhamnosus, Lactobacillus delbruecki* (otherwise known as *Lactobacillus bulgaricus*), *Lactobacillus paracasei, Lactobacillus salivarius, Lactoba-*

*cillus casei*, *Bifidobacterium lactis*, *Bifidobacterium longum*, *Bifidobacterium breve*, and *Streptococcus* thermophiles.

Optionally, the disclosed topical compositions may include additional bacterial species or non-bacterial species that natural occur in honey (e.g. yeasts), products of fermentation (e.g. lactic acid and/or ethanol), peroxides and any other metabolic byproducts of the bacteria listed above, or of those organisms contained in honey, and additional carriers, buffers, emulsifiers, and anti-oxidants.

Additional components for the disclosed topical compositions may include, but are not limited to plant-based products. In some embodiments, the one or more plant-based products are present in the topical composition at a concentration of at least about 5%, 10%, 20%, 30%, 40%, 50%, 55%, 60%, 65%, 70%, 75%, 80%, 85%, 90% or higher, or within a concentration range bounded by any of these values (e.g., 30-90% (w/w), or about 30-70% (w/w), or about 30-50% (w/w)).

Suitable plant-based products for the disclosed topical compositions may include plant-based lipid products. Plant-based lipid products may include plant-based butters (such as shea butter or cocoa butter), plant-based waxes (such as carnauba wax or beeswax), and plant-based oils (such as coconut oil, sunflower oil, or jojoba oil, or fractions thereof).

Suitable plant-based products for the disclosed topical compositions may include plant-based gels, lotions, or other extracts or components. In some embodiments, the disclosed composition comprise a plant-based gel, lotion, or other extract or component from the Aloe vera plant or a plants producing similar substances as the Aloe vera plant.

Additional plant-based components for the disclosed topical compositions may include turmeric (e.g., *Curcuma longa*), turmeric-derived products, or components that are present in turmeric. In some embodiments, the disclosed compositions include turmeric powder and/or components that are present in turmeric such as curcuminoids and essential oils. The disclosed compositions may include components selected from but not limited to curcumin, demethoxycurcumin, and bisdemethoxycurcumin. The disclosed compositions may include components selected from but not limited to turmerone, germacrone, atlantone, and zingiberene. In some embodiments, the disclosed compositions comprise turmeric-derived products, or components that are present in turmeric at a concentration of at least about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% or higher, or within a concentration range bounded by any of these values (e.g., about 0.5-10% (w/w) or about 2.0-6.0% (w/w)).

The disclosed topical compositions may comprise curcuminoids or essential oils (e.g., curcuminoids and essential oils that are present in turmeric (such as curcumin, demethoxycurcumin, and bisdemethoxycurcumin; and turmerone, germacrone, atlantone, and zingiberene)). In some embodiments, the curcuminoids and/or essential oils are present in the composition at a concentration of at least about 0.005%, 0.01%, 0.02%, 0.05%, 0.1%, 0.2%, 0.5% or higher, or within a concentration range bounded by any of these values (e.g., about 0.005-0.5% (w/w) or 0.05-0.5% (w/w)).

Additional plant-based components for the disclosed topical compositions may include, but are not limited to beta-glucans, olive polyphenols, ahi flower oil, carotenoids such as fucoxanthin, ceramides, and fatty acids such as omega-7 oil optionally obtained from sea buckthorn.

The disclosed topical compositions may comprise micronutrient components, including but limited to vitamins. Suitable vitamins may include, but are not limited to vitamin B12, vitamin E and/or vitamin B3. In some embodiments, the micronutrient (e.g., vitamin B12, vitamin E and/or vitamin B3) is present in the topical composition at a concentration of at least about 0.1%, 0.2%, 0.5%, 1.0%, 1.5%, 2.0%, 2.5%, 3.0%, 3.5%, 4.0%, 4.5%, 5.0%, 5.5%, 6.0% or higher, or within a concentration range bounded by any of these values (e.g., about 0.1-5% (w/w) or about 1-3% (w/w)).

The disclosed topical compositions may comprise a humectant. Suitable humectants may include, but are not limited to glycerin, or other fractions of triglyceride hydrolysis. In some embodiments, the disclosed compositions comprise glycerin (or other fractions of triglyceride hydrolysis) at a concentration of about 1%, 2%, 3%, 5%, 10%, 15%, 20%, 25%, 30% or higher, or within a concentration range bounded by any of these values (e.g., 3-30% (w/w), or about 5-25% (w/w), or about 10-20% (w/w), or about 15% (w/w)).

The disclosed topical compositions may comprise emulsifiers. Suitable emulsifiers may include, but are not limited to, plant-based emulsifiers such as lecithin, especially from *Helianthus annuus*.

The disclosed topical compositions may include anti-oxidants. Suitable anti-oxidants may include, but are not limited to, hydroxytyrosol.

Additional components for the disclosed topical compositions may include, but are not limited to beta-glucans, olive polyphenols, ahi flower oil, carotenoids such as fucoxanthin, ceramides, and fatty acids such as omega-7 oil optionally obtained from sea buckthorn.

The disclosed topical compositions preferably are formulated to be supportive and compatible with the skin microbiome and pH. For example, preferably the disclosed topical compositions have a pH within a range of 6-8. Optionally, the disclosed topical compositions may include a buffering system.

The disclosed topical compositions may be produced by methods known in the art including, but not limited to the following description. This description is not meant to limit future or potential means of production or the claimed subject matter, nor to exhaustively detail all methods currently in use or development. Neither the set of ingredients used in the following description, nor their relative amounts, should be interpreted to limit the claimed subject matter.

A base vehicle comprising honey, shea butter, cocoa butter, and glycerin may be prepared as follows. To an amount of shea butter that consists of 50% of the final formulation by mass, there may be added an amount of softened cocoa butter equal to 25% of the final formulation by mass. After creating a homogenous cream via stirring or blending, an amount of glycerin and honey, equal to 12.5% and 5% of the final formulation by mass, respectively, may be added to the cocoa and shea butter mixture.

A blend containing bacteria from the genera *Lactobacillus*, *Bifidobacterium*, or *Streptococcus*, especially as listed above among, may be dissolved in a solution of distilled water, along with sunflower lecithin, that together are equal to 2.5% of the final formulation by mass. This water-based mixture then may be added to the base vehicle above.

Lastly, sunflower oil and fractioned coconut oil, each in an amount equal to 2.5% of the final formulation by weight, may together be dissolved in the base vehicle above and mixed on low power until integrated to yield a cream-like solution. The resulting product should be refrigerated for 12 to 24 hours. Depending on the crystal structure of the cocoa butter used, applying heat and controlling re-solidification conditions may be necessary to optimize consistency. Preparation may be best conducted slightly above average room temperature, depending on environment and ingredient feedstock. The vehicle and bacterial preparations detailed herein may be adapted for application to other body systems, including for different purposes entirely.

ILLUSTRATIVE EMBODIMENTS

The following embodiments are illustrative and should not be interpreted to limit the scope of the claimed subject matter.

Embodiment 1

A topical composition for skin comprising bacteria and honey.

Embodiment 2

The topical composition of embodiment 1, wherein the bacteria is live bacteria.

Embodiment 3

The topical composition of embodiment 1, wherein the bacteria is killed bacteria.

Embodiment 4

The topical composition of embodiment 3, wherein the killed bacteria is killed by a method selected from heat treatment, irradiation, chemical treatment, and a combination thereof.

Embodiment 5

The topical composition of any of the foregoing embodiments, wherein the bacteria are present in the topical composition at a concentration of at least about $10^4$, $10^5$, $10^6$, $10^7$, $10^8$ colony forming units (CFU)/gram (g) topical composition or higher, or within a concentration range bounded by any of these values (e.g., $10^4$-$10^8$ CFU/g).

Embodiment 6

The topical composition of any of the foregoing embodiments, wherein the honey is selected from Manuka honey, raw honey, refined honey, and a combination thereof.

Embodiment 7

The topical composition of any of the foregoing embodiments, wherein the honey is present in the topical composition at a concentration of at least about 10%, 15%, 20%, 25%, 30%, 35%, 40%, 45%, 50%, 55%, 60%, 65%, 70% (w/w) or higher, or within a range bounded by any of these values (e.g. about 15-60% (w/w) or 20-50% (w/w)).

Embodiment 8

The topical composition of any of the foregoing embodiments, wherein the bacteria belong to the genus *Lactobacillus*.

Embodiment 9

The topical composition of any of the foregoing embodiments, wherein the bacteria belong to a species selected from *Lactobacillus acidophilus*, *Lactobacillus plantarum*, *Lactobacillus rhamnosus*, *Lactobacillus delbruecki* (otherwise known as *Lactobacillus bulgaricus*), *Lactobacillus paracasei*, *Lactobacillus salivarius*, and *Lactobacillus casei*.

Embodiment 10

The topical composition of any of the foregoing embodiments, wherein the bacteria belong to the genus *Bifidobacterium*.

Embodiment 11

The topical composition of any of the foregoing embodiments, wherein the bacteria belong to a species selected from *Bifidobacterium lactis*, *Bifidobacterium longum*, and *Bifidobacterium breve*.

Embodiment 12

The topical composition of any of the foregoing embodiments, wherein the bacteria belong to the genus *Streptococcus*.

Embodiment 13

The topical composition of any of the foregoing embodiments, wherein the bacteria are *Streptococcus* thermophiles.

Embodiment 14

The topical composition of any of the foregoing embodiments, further comprising one or more micro-nutrients (e.g., a vitamin such as vitamin B12 and/or vitamin E).

Embodiment 15

The topical composition of any of the foregoing embodiments, further comprising vitamin B12.

Embodiment 16

The topical composition of embodiment 15, wherein vitamin B12 is present in the topical composition at a concentration of at least about 0.1%, 0.2%, 0.5%, 1.0%, 1.5%, 2.0%, 2.5%, 3.0%, 3.5%, 4.0%, 4.5%, 5.0%, 5.5%, 6.0% or higher, or within a concentration range bounded by any of these values (e.g., about 0.1-5% (w/w) or about 1-3% (w/w)).

Embodiment 17

The topical composition of any of the foregoing embodiments, further comprising turmeric and/or derivatives of turmeric such as curcuminoids or essential oils.

Embodiment 18

The topical composition of embodiment 17, wherein turmeric is present in the topical composition at a concentration of at least about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% or higher, or within a concentration range bounded by any of these values (e.g., about 0.5-10% (w/w) or about 2.0-6.0% (w/w)).

Embodiment 19

The topical composition of any of the foregoing embodiments, further comprising curcuminoids or essential oils.

Embodiment 20

The topical composition of embodiment 19, wherein the curcuminoids and/or essential oils are present in the composition at a concentration of at least about 0.005%, 0.01%, 0.02%, 0.05%, 0.1%, 0.2%, 0.5% or higher, or within a concentration range bounded by any of these values (e.g., about 0.005-0.5% (w/w) or 0.05-0.5% (w/w)).

Embodiment 21

The topical composition of any of the foregoing embodiments, further comprising one or more plant lipids, optionally provided by or present in one or more of shea butter, cocoa butter, coconut oil, sunflower oil, and mixtures thereof.

Embodiment 22

The topical composition of embodiment 21, wherein the one or more plant lipids are present in the topical composition at a concentration of at least about 10%, 20%, 30%, 40%, 50%, 55%, 60%, 65%, 70%, 75%, 80%, 85%, 90% or higher, or within a concentration range bounded by any of these values (e.g., 30-90% (w/w), or about 30-70% (w/w), or about 30-50% (w/w)).

Embodiment 23

The topical composition of any of the foregoing embodiments, further comprising one or more of shea butter, cocoa butter, and a mixture thereof.

Embodiment 24

The topical composition of any of the foregoing embodiments, further comprising one or more of coconut oil, sunflower oil, and a mixture thereof.

Embodiment 25

The topical composition of any of the foregoing embodiments, further comprising a humectant.

Embodiment 26

The topical composition of embodiment 25, wherein the humectant is glycerin.

Embodiment 27

The topical composition of claim 26, wherein the glycerin is present in the composition at a concentration of about 1%, 2%, 3%, 5%, 10%, 15%, 20%, 25%, 30% or higher, or within a concentration range bounded by any of these values (e.g., 3-30% (w/w), or about 5-25% (w/w), or about 10-20% (w/w), or about 15% (w/w)).

Embodiment 28

The composition of embodiment 1, further comprising one or more components selected from the group consisting of beta-glucans, hydroxytyrosol, olive polyphenols, ahi flower oil, carotenoids such as fucoxanthin, ceramides, and fatty acids such as omega-7 oil optionally obtained from sea buckthorn.

Embodiment 29

A method of treating a skin condition, the method comprising applying the topical composition of any of the foregoing embodiment to the skin.

Embodiment 30

The method of embodiment 29, wherein the skin condition selected from the group consisting of dry skin, dermatitis, eczema, or a combination thereof.

Embodiment 31

The method of embodiment 29, wherein the skin condition is atopic dermatitis.

Embodiment 32

A method of treating a scalp condition and/or hair condition, the method comprising applying the topical composition of any of embodiments 1-28 to the scalp and/or hair.

Embodiment 33

The method of embodiment 32, wherein the scalp condition and/or hair condition is selected from the group consisting of dry scalp, dandruff, psoriasis, cradle cap, seborrheic dermatitis, eczema, and combinations thereof.

Embodiment 34

The method of embodiment 32, wherein scalp condition is seborrheic dermatitis.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Twenty (20) subjects were enrolled to assess a skin cream product and a hair tonic product for comfort and safety. The compositions of the skin cream product and the hair tonic product are as follows:

TABLE 1

| Component | Skin Cream Product | Hair Tonic Product |
| --- | --- | --- |
| Honey | 3 g (~5% (w/w)) | 41 g (~47% (w/w)) |
| Shea Butter | 30 g (~46% (w/w)) | 4 g (~5% (w/w)) |
| Cocoa Butter | 15 g (~23% (w/w)) | — |
| Glycerin | 9 g (~14% (w/w)) | 15 g (~17% (w/w)) |
| Coconut Oil | 1.5 g (~2% (w/w)) | 6 g (~7% (w/w)) |
| Sunflower Oil | 1.5 g (~2% (w/w)) | — |
| Vitamin B12 | 0.5 g (~1% (w/w)) | 1 g (~1% (w/w)) |
| Vitamin E | 0.5 g (~1% (w/w)) | 0.5 g (~0.5% (w/w)) |
| Sunflower Lecithin | — | 3 g (~3% (w/w)) |
| Water | — | 14 g (~16% (w/w)) |
| *Lactobacillus* spp. | 4.5 g (~7% (w/w)) | 3 g (~3% (w/w)) |
| Total | 65.5 g | 87.5 g |

The average age of the subjects was 39 (range 10-72) with 10 men and 10 women. Three male and three female subjects also had both skin eczema and dry scalp.

All subjects were instructed to use the skin cream product and the hair tonic product once a day for ten days. The skin cream was to be applied in a thin layer to arms and legs in the morning after a shower. The hair tonic was to be applied to the scalp once a day for seven days. Prior to taking a shower in the morning, a palm-size amount of the hair tonic was to be massaged into the scalp, left in place for about five minutes, and then rinsed in the shower.

A brief questionnaire was conducted on all the subjects after the study. All subjects reported using the product as instructed. No subjects reported any adverse reactions. A questionnaire scale of 1 to 4 was used, with 1 being poor and 4 being excellent. The results are noted in the Table 2.

TABLE 2

| Parameter | Skin Cream Product | Hair Tonic Product |
| --- | --- | --- |
| Ease of Application | 4.0 | 3.95 |
| Adverse Reactions | 0 | 0 |
| Feel on Skin/Scalp | 3.9 | 3.9 |

One of the subjects found the skin cream slightly greasy and gave a rating of 3. Two of the subjects found the hair tonic to be slightly sticky and gave a rating of 3. The 6 subjects who had skin eczema and dry scalp all reported a subjective improvement in the quality of their skin.

Example 2

A hair tonic and a skin cream were prepared with the following components:

Hair Tonic. Vitamin B12: 2%; Turmeric: 4%; Honey: 43%; Base (inactive ingredients): 51%; Bacteria (Heat-killed *Lactobacillus Acidophilus*): 1 million colony forming units per gram of product; and Bacteria (Heat-killed *Lactobacillus Plantarum*): 1 million colony forming units per gram of product.

Skin Cream. Vitamin B12: 2%; Turmeric: 4%; Honey: 30%; Base (inactive ingredients): 64%; Bacteria (Heat-killed *Lactobacillus Acidophilus*): 1 million colony forming units per gram of product; and Bacteria (Heat-killed *Lactobacillus Plantarum*): 1 million colony forming units per gram of product.

Twenty (20) adult and seventeen (17) pediatric subjects with seborrheic dermatitis were enrolled to study the hair tonic, and twenty (20) adult and twenty (20) pediatric subjects with atopic dermatitis were enrolled to study the skin cream. All subjects were instructed to use the skin cream product and the hair tonic product once a day for ten days. The skin cream was to be applied in a thin layer to arms and legs in the morning after a shower. The hair tonic was to be applied to the scalp once a day for ten days. Prior to taking a shower in the morning, a palm-size amount of the hair tonic was to be massaged into the scalp, left in place for about five minutes, and then rinsed in the shower.

A brief questionnaire was conducted on all the subjects after the study. All subjects reported using the product as instructed. No subjects reported any adverse reactions. A questionnaire scale of 1 to 4 was used, with 1 being poor and 4 being excellent. The results are presented in Table 3:

TABLE 3

| Parameter | Skin Cream Product | Hair Tonic Product |
| --- | --- | --- |
| Ease of Application | 4.0 | 3.95 |
| Adverse Reactions | 0 | 0 |
| Feel on Skin/Scalp | 3.9 | 3.9 |
| Improvement of dermatitis | 4.0 | 4.0 |

Example 3: Topical Treatment for Dandruff & Dry Scalp

A scalp mask product were prepared with the following components:

BASE (inactive ingredients; 51%): Water, behentrimonium methosulfate and cetearyl alcohol, cetyl alcohol, centrimonium chloride, dimethicone, capric triglyceride, aloe vera, sunflower seed, jojoba oil, *quinoa*, shea butter, potassium sorbate, panthenol, hydroxypropyltrimonium chloride ACTIVE INGRDIENTS: Organic Honey (45%), Organic Turmeric (4%), Bacteria (Heat-killed *Lactobacillus Acidophilus*): 1 million colony forming units per gram of product, Bacteria (Heat-killed *Lactobacillus Plantarum*): 1 million colony forming units per gram of product and Bacteria (Heat-killed *Lactobacillus Bulgaricus*): 1 million colony forming units per gram of product.

TABLE 4

| Protocol: 100 ml Bacteria solution and inactivation by Autoclave Bacteria Strains | Concentration (CFU/g) | Target concentration for mix with Yobee component (CFU/g) |
| --- | --- | --- |
| *Lactobacillus plantarum* (L. plantarum) | 400 billion | 1 million[1] |
| *Lactobacillus acidophilus* (L. acidafphilus) | 200 billion | 1 million |
| *Lactobacillus bulgaricus* (L. bulgaricus) | 50 billion | 1 million |

[1] For YoBee Component mixture add 10 µl of bacteria solution for each gram of component. 10 µl of bacteria solution = 1,000,000 CFUs Procedure:

1. A 100 ml of bacteria solution were prepared so that the final concentration was 100,000 CFUs of bacteria per 1 µl of sterile phosphate buffered saline (PBS)[2].

[2] Alfa Aesar brand Phosphate-buffered saline (PBS, 10X) at pH 7.4 diluted down to 1X was used.

2. The solution was sterilized by autoclave and allowed to cool down to room temperature. Autoclave conditions were: 100° C. (212° F.) for 10 minutes.

3. 100 µl of each of the autoclaved bacteria suspensions were then plated onto MRS agar plates. (Positive controls were set in which the bacteria was suspended in PBS, but not autoclaved).

4. Plates were then loaded into ajar that was charged with an anaerobic gas mixture, sealed tightly, and then incubated at 37° C.

5. After 3 days of incubation plates were inspected for growth.

6. The bacteria was considered inactivated if not growth is observed in the plates with autoclaved bacteria and growth is observed the plates with bacteria that was not autoclaved.

NOTE: The *lactobacillus* suspension is being prepared each time a new batch of final product is being made.

Applicants applied a palm-sized amount of the scalp mask product to the scalp in a single application.

The scalp mask product contains: Base (inactive ingredients): 51%, Honey: 45%, Turmeric: 4%, Bacteria (Heat-killed *Lactobacillus Acidophilus*): 1 million colony forming units per gram of product, Bacteria (Heat-killed *Lactobacillus Plantarum*): 1 million colony forming units per gram of product, Bacteria (Heat-killed *Lactobacillus Bulgaricus*): 1 million colony forming units per gram of product. The final weight of the product is estimated at 3817.03 grams.

The study was conducted as an Investigational New Drug with the FDA with approval from our Institutional IRB. Inclusion criteria were adults 18 and older with dry scalp and dandruff symptoms as determined by a trained research physician. Patients diagnosed with other scalp diseases such as psoriasis, tinea capitis, and pediculosis capitis, used systemic steroid or oral antibiotics in the past two months or had an allergy to any of the preparation components were excluded. Thirty-five adults (55% female, 40% White, 50% Asian, 5% Black, 5% Multiracial) with dry scalp were recruited and followed for this 2-week study. Participant median age was 26; IQR=8 years, range=20-78. The initial study visit consisted of a scalp exam and scalp photographs by a trained research physician to confirm that each participant had a dry scalp condition. At this time participants completed an intake survey including assessment of the participant demographics as well as the standardized assessments of scalp condition history and current symptoms described below. The scalp exam, photographs and intake survey provided the basis for our initial evaluation of disease and symptom severity through the Investigator Global Assessment (IGA), Total Severity Score (TSS) and Scalpdex. The IGA is a 5-point validated instrument that rates overall disease severity according to the following categories: 0=clear, 1=almost clear, 2=mild disease, 3=moderate disease, 4=severe disease. The TSS represents the sum of erythema, scaling, and pruritus severity scores of the scalp disease. A minimum TSS score is 0 (none) and the maximum TSS score is 9 (severe). Scalpdex is a validated 23-item quality-of-life questionnaire that is completed by participants to measure their subjective improvement with treatment.

Participants were instructed to liberally apply the scalp mask product to their scalp once daily for 14 days, leave in place for at least 7 minutes, and rinse in the shower. Participants returned after 14 days of treatment for an in-person follow up including a physician scalp assessment, end photograph and exit survey. At that point, the IGA, TSS and Scalpdex were again determined.

Results from paired t-tests with one-sided p-values found that after 2 weeks of treatment, overall disease severity by IGA decreased from 2.1 at baseline to 1.1 at the end of the trial ($t(34_{df})$=8.15; p<0.001). Additionally, mean TSS scores fell from 3.5 at baseline to 1.8 at the conclusion ($t(34_{df})$=p<0.001). Overall Scalpdex decreased from 46.0 to 39.5 ($t(33_{df})$=3.4; p=0.001, reflecting significant reductions in the subjective quality of life burden associated with the scalp condition (Table 5). Notably, significant decreases were observed for all three TSS subscales (Perythema<0.001; Pscaling<0.001; Ppruritis<0.001) as well as all three Scalpdex subscales (Psymptoms=0.001; Pemotion <0.001; Pfunctioning=0.04) (Tables 5 and 6). Additionally, the intervention was well-tolerated, without adverse effects or complaints reported by any study participants.

Overall, the preliminary data found that use of the topical dry scalp product clinically reduced the symptoms and disease severity of dry scalp conditions, improved patient—reported quality of life within all assessed domains, and had no adverse effects in adults. These results are promising and build upon our understanding of how treatments targeting the skin microbiome. Future randomized controlled trials will shed further light upon the safety and efficacy of this novel product and help identify the populations most likely to benefit.

TABLE 5

IGA, TSS and Scalpdex Scores Before and After Intervention

|  | Baseline Mean(SD) | After Intervention Mean(SD) | P value |
|---|---|---|---|
| IGA Score | 2.1 (0.6) | 1.1 (0.8) | <0.001 |
| TSS Score | 3.5 (1.4) | 1.8 (1.0) | <0.001 |
| Erythema | 1.8 (0.7) | 1.3 (0.5) | <0.001 |
| Scaling | 2.4 (0.7) | 1.8 (0.6) | <0.001 |
| Pruritis | 2.4 (0.7) | 1.7 (0.6) | <0.001 |
| Scalpdex Score | 46.0 (13.4) | 39.5 (10.3) | <0.001 |

TABLE 6

Scalpdex Score Subscales Before and After Intervention

|  | Baseline Mean(SD) | After Intervention Mean(SD) | P value |
|---|---|---|---|
| Symptom severity | 46.5 (15.3) | 39.0 (10.5) | <0.001 |
| Emotional impact | 48.6 (14.8) | 40.9 (11.3) | <0.001 |
| Functional impact | 37.9 (13.6) | 34.5 (11.1) | 0.04 |

All publications and patent applications mentioned in this specification are herein incorporated by reference to the same extent as if each individual publication or patent application was specifically and individually indicated to be incorporated by reference.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

What is claimed is:

1. A scalp mask cream for treating a dry scalp condition comprising the scalp mask cream including killed *Lactoba-* cillus acidophilus, killed Lactobacillus plantarum, killed Lactobacillus bulgaricus, and honey, wherein the scalp mask cream is applied to the scalp to treat a dry scalp condition.

2. The scalp mask cream of claim 1, wherein the killed bacteria is killed by a method selected from heat treatment, irradiation, chemical treatment, and a combination thereof.

3. The scalp mask cream of claim 1, wherein the bacteria are present in the scalp mask cream at a concentration of about $10^4$-$10^8$ colony forming units/gram before being killed.

4. The scalp mask cream of claim 1, wherein the honey is selected from Manuka honey, raw honey, refined honey, and a combination thereof, and optionally wherein the honey is present in the composition at a concentration of about 15-60% (w/w).

5. The scalp mask cream of claim 1, further comprising, killed Bifidobacterium lactis, or killed Streptococcus thermophiles.

6. The scalp mask cream of claim 1, further comprising killed bacteria belonging to a species selected from Lactobacillus rhamnosus, Lactobacillus delbruecki, Lactobacillus paracasei, Lactobacillus salivarius, and Lactobacillus casei.

7. The scalp mask cream of claim 1, further comprising killed bacteria belonging to a species selected from Bifidobacterium lactis, Bifidobacterium longum, and Bifidobacterium breve.

8. The scalp mask cream of claim 1, further comprising killed bacteria are Streptococcus thermophiles.

9. The scalp mask cream of claim 1, further comprising one or more micro-nutrients.

10. The scalp mask cream of claim 1, further comprising vitamin B12, optionally wherein the vitamin B12 is present in the scalp mask cream at a concentration of about 0.1-5% (w/w).

11. The scalp mask cream of claim 1, further comprising turmeric, optionally wherein turmeric is present in the scalp mask cream at a concentration of about 0.5-10% (w/w).

12. The scalp mask cream of claim 1, further comprising curcuminoids or essential oils, optionally wherein the curcuminoids or essential oils are present in the composition at a concentration of about 0.005-0.5%.

13. The scalp mask cream of claim 1 further comprising one or more plant lipids, optionally wherein the one or more plant lipids are present in the composition at a concentration of at least 20% (w/w).

14. The scalp mask cream of claim 1, further comprising one or more of shea butter, cocoa butter, one or more of coconut oil, sunflower oil, or mixtures thereof.

15. The scalp mask cream of claim 1, further comprising a humectant, optionally wherein the humectant is glycerin and the glycerin is present in the composition at a concentration of about 3-30% (w/w).

16. The scalp mask cream of claim 1, further comprising one or more components selected from the group consisting of beta-glucans, hydroxytyrosol, olive polyphenols, ahi flower oil, carotenoids including fucoxanthin, ceramides, and fatty acids including omega-7 oil optionally obtained from sea buckthorn.

17. A skin cream for treating a scalp condition comprising bacteria, turmeric, and honey, wherein the bacteria comprise killed Lactobacillus acidophilus, killed Lactobacillus delbruecki, and killed Lactobacillus plantarum wherein the skin cream is applied to the scalp to treat a dry scalp condition.

18. A skin-cream for treating a scalp condition, comprising bacteria, turmeric, Vitamin B12, and honey, wherein the bacteria comprise killed Lactobacillus acidophilus, killed Lactobacillus delbruecki, and killed Lactobacillus plantarum and the skin cream is used to treat dry scalp, skin or hair.

19. The skin cream of claim 18, wherein the skin cream further comprises shea butter, glyceryl stearate, and cetearyl alcohol.

20. The scalp mask cream of claim 1, wherein the scalp mask cream further comprises cetearyl alcohol, shea butter, and caprylic/capric triglycerides.

* * * * *